United States Patent
Bonanno et al.

(10) Patent No.: US 12,336,802 B2
(45) Date of Patent: Jun. 24, 2025

(54) METHOD AND SYSTEM FOR SIMULTANEOUS MAPPING OF QUANTITATIVE MRI PARAMETERS USING A T2 PREPARED INVERSION

(71) Applicants: Siemens Healthcare GmbH, Erlangen (DE); STICHTING RADBOUD UNIVERSITEIT, Nijmegen (NL)

(72) Inventors: Gabriele Bonanno, Bern (CH); Jose Pedro Marques, Nijmegen (NL); Tobias Kober, Lausanne (CH); Tom Hilbert, Lausanne (CH)

(73) Assignees: Siemens Healthcare GmbH, Erlangen (DE); Stichting Radboud Universiteit, Nijmegen (NL)

( * ) Notice: Subject to any disclaimer, the term of this patent is extended or adjusted under 35 U.S.C. 154(b) by 71 days.

(21) Appl. No.: 18/300,604

(22) Filed: Apr. 14, 2023

(65) Prior Publication Data

US 2023/0329576 A1  Oct. 19, 2023

(30) Foreign Application Priority Data

Apr. 14, 2022 (EP) .................................. 22168303

(51) Int. Cl.
*A61B 5/055* (2006.01)
*A61B 5/00* (2006.01)
(Continued)

(52) U.S. Cl.
CPC ............ *A61B 5/055* (2013.01); *A61B 5/0042* (2013.01); *G01R 33/50* (2013.01);
(Continued)

(58) Field of Classification Search
CPC ...... A61B 5/055; A61B 5/0042; G01R 33/50; G01R 33/5602; G01R 33/243;
(Continued)

(56) References Cited

U.S. PATENT DOCUMENTS 10,761,171 B2    9/2020  Gulani et al.
2023/0194641 A1*  6/2023  Nezafat .............. G01R 33/5608
                                                                324/309

OTHER PUBLICATIONS

Nezafat Reza, et al., B1 insensitive T2 preparation for improved coronary magnetic resonance angiography at 3T. Magnetic Resonance in Medicine 55:858-864 (2006); 2006.
(Continued)

*Primary Examiner* — Rishi R Patel
(74) *Attorney, Agent, or Firm* — Laurence A. Greenberg; Werner H. Stemer; Ralph E. Locher (57) ABSTRACT

A qMRI system and method map qMRI parameters of a biological object. The method includes performing, by the qMRI system, N scans wherein each scan, includes: performing T2-prepared inversion pulse series, each followed by readout blocks, each magnetization preparation RF pulse series is a T2-prepared inversion pulse series containing multiple pulses and an inter-pulse duration, for varying to obtain different T2 weightings; and acquiring, by the MRI system and during each readout block of an MRI, a recovery signal generated by a part of the biological object, wherein for each readout block, an MRI signal is acquired by the MRI system at different inversion times. An image of the part is reconstructed for and from each MRI signal. A voxel-wise signal is created by concatenating intensity values for a same voxel for the reconstructed images. A physical model is fitted to the concatenated intensity values to obtain a qMRI map.

13 Claims, 4 Drawing Sheets

(51) Int. Cl.
  *G01R 33/24* (2006.01)
  *G01R 33/50* (2006.01)
  *G01R 33/56* (2006.01)
(52) U.S. Cl.
  CPC ........ *G01R 33/5602* (2013.01); *G01R 33/243* (2013.01); *G01R 33/246* (2013.01)
(58) Field of Classification Search
  CPC ................ G01R 33/246; G01R 33/288; G01R 33/4824; G01R 33/4826; G01R 33/4828; G01R 33/561; G01R 33/5613; G01R 33/5614; G01R 33/56341; G01R 33/56366; G01R 33/58; G01R 33/4822; G01R 33/5611; G01R 33/5616; G01R 33/5608
  See application file for complete search history.

(56) References Cited

OTHER PUBLICATIONS

Gabriele, Bonanno et al: "High-resolution T2 maps of the whole brain at 7 Tesla: a proof of concept study using adiabatic T2-prepared Flash and compressed sensing"; Proceedings of The 2021 ISMRM & SMRT, Annual Meeting & Exhibition, May 15-20, 2021; ISMRM, 2030 Addison Street; 7$^{th}$ Floor, Berkeley, CA 94704 USA; No. 3047; Apr. 30, 2021; XP040725066.

Marques JP, et al., MP2RAGE, a self bias-field corrected sequence for improved segmentation and T1-mapping at high field. Neuroimage—2010;49(2):1271-1281.

Frahm J, Haase et al., Rapid NMR imaging of dynamic processes using the Flash technique. Magn Reson Med 1986;3(2):321-327.

Forman C, et al, High-resolution 3D whole-heart coronary MRA: a study on the combination of data acquisition in multiple breath-holds and 1D residual respiratory motion compensation. MAGMA 2014.

Deoni SC, et al., Rapid combined T1 and T2 mapping using gradient recalled acquisition in the steady state. Magn Reson Med 2003;49(3):515-526.

Ma D, et al., Magnetic resonance fingerprinting. Nature 2013;495(7440):187-192.

Giri S, et al., T2 quantification for improved detection of myocardial edema. Journal of Cardiovascular Magnetic Resonance 2009;11:56 doi:10.1186/1532-429X-11-56; 2009.

Caan, M.W.A.: mapping in one sequence at 7 Tesla; Proceedings of The International Society for Magnetic Resonance in Medicine, Joint Annual Meeting ISMRM-ESMRMB, No. 34, Jun. 1, 2018; XP040699243; Paris, France.

Ji, Sooyeon et al: "Quad-Contrast Imaging:Simultaneous Acquisition of Four Contrast-Weighted Images (PD-Weighted, T2-Weighted, PD-Flair and T2-Flair Images) With Synthetic TI-Weighted Image, TI- and T2-Maps"; IEEE Transactions on Medical Imaging; IEEE, USA; vol. 40, No. 12, Jun. 30, 2021;pp. 3617-3626; XP011890417; ISSN: 0278-0062; DOI: 10.1109/TMI.2021.3093617.

Heule, R.: "Simultaneous Mapping of Longitudinal and Transverse Relaxation Times"; Proceedings of The International Society for Magnetic Resonance in Medicine; No. E920; Jul. 24, 2020; XP040718969.

Mugler III JP, et al., Three-dimensional magnetization-prepared rapid gradient-echo imaging (3D MP Rage). Magn Reson Med 1990;15(1):152-157.

Brittain JH, et al., Coronary angiography with magnetization-prepared T2 contrast. Magn Reson Med 1995;33(5):689-696.

Ruud B. Van Heeswijk, PHD, et al, Free-Breathing 3 T Magnetic Resonance T2-Mapping of the Heart, JACC: Cardiovascular Imaging vol. 5, No. 12, 2012, © 2012 by The American College of Cardiology Foundation ISSN 1936-878X/$36.00, Published by Elsevier Inc. http://dx.doi.org/10.1016/j.jcmg.2012.06.010; 2012.

Forman C, et al., High-resolution 3D whole-heart coronary MRA: a study on the combination of data acquisition in multiple breath-holds and 1D residual respiratory motion compensation. Magma 2014, DOI 10.1007/s10334-013-0428-x, Received: Jul. 19, 2013 / Revised: Dec. 9, 2013 / Accepted: Dec. 16, 2013 ESMRMB 2014; 2013.

Wetzl J, et al., High-resolution dynamic CE-MRA of the thorax enabled by iterative Twist reconstruction. Magn Reson Med 2017;77(2):833-840.

Cloos Ma, et al., Multiparametric imaging with heterogeneous radiofrequency fields, Received Aug. 10, 2015, Accepted Jul. 1, 2016, Published Aug. 16, 2016, Nat Commun 2016;7:12445.

* cited by examiner

METHOD AND SYSTEM FOR SIMULTANEOUS MAPPING OF QUANTITATIVE MRI PARAMETERS USING A T2 PREPARED INVERSION

CROSS-REFERENCE TO RELATED APPLICATION

This application claims the priority, under 35 U.S.C. § 119, of European Patent Application EP 22168303.0, filed Apr. 14, 2022; the prior application is herewith incorporated by reference in its entirety.

FIELD AND BACKGROUND OF THE INVENTION

The present invention falls within the field of magnetic resonance imaging (MRI) systems and methods. In particular, the present invention relates to a method and system for magnetic resonance imaging in which a simultaneous mapping of quantitative MRI parameters is carried out using a T2 prepared inversion magnetization preparation, and to a device for carrying out the method.

Quantitative MRI (qMRI) plays an important role in the study of tissue-specific and organ-specific pathologies and has been widely adopted to support diagnosis, monitor therapy and interventions in many clinical applications. The main goal of qMRI techniques is to estimate tissue-specific parameters with minimal experimental bias. The estimation of an "absolute" MR tissue property has high interest because it may allow to detect pathological tissue as well as it could be used to follow-up pathological conditions for a single patient, compare patient groups, or compare single patient outcomes to normative values. Additionally, the measure of tissue properties is sought to be independent of the scanner hardware being used.

Conventional gMRI methods use analytical solutions of spin evolutions to estimate tissue properties (e.g., T1 and T2 relaxation parameters in MRI). These techniques typically implement a series of inversion-recovery or saturation-recovery measurements to estimate the longitudinal (spin-lattice) relaxation time, T1, and spin-echo measurements to estimate the transverse (spin-spin) relaxation time, T2. Although such measurements can provide excellent results and are often used as ground-truth, they require long acquisition times (TA) that are impractical for use in routine clinical examinations. Therefore, alternative methods have been introduced to determine T1 and T2 more rapidly. However, high isotropic spatial resolution and large volume coverage are still limited by long TA and/or signal-to-noise-ratio. Additionally, most of these methods are tailored to estimate a single MR parameter at a time and, in turn, their results are often biased by physical mechanisms that are not accounted for in the model.

Over the last two decades, research has focused on gMRI techniques to simultaneously estimate T1 and T2 for increased accuracy and reduced experimental bias and acquisition time. In particular, a first method, DESPOT1/2 by Deoni et al. [1], uses variable flip angles to drive longitudinal and transversal magnetization to steady state with a spoiled gradient echo sequence to estimate T1 and subsequently with a steady-state free precession sequence for T2. While DESPOT1/2 is faster than conventional methods and offers high signal-to-noise ratio, its analytical solution may still suffer from experimental bias. A second method, called MR fingerprinting (MRF), had an important impact in the MRI community (Ma et al. [2], U.S. Pat. No. 8,723,518 B2). MRF introduced a paradigm shift from steady-state sequences to transient states achieved by continuously changing sequence parameters and, therefore, from analytical solutions to physics-based numerical models of those unique signal evolutions. By doing so, MRF deliberately entangles relaxation parameters evolution with unique experimental conditions and uses dictionary fitting to estimate tissue properties. The many degrees of freedom of MRF enable fast and simultaneous estimation of tissue properties. However, accuracy of such estimates may be limited by experimental factors mainly related to the non-conventional fast sequences used for the acquisition.

Another technique relevant for the present invention is the magnetization-prepared rapid gradient echo (MPRAGE) technique [3], In this context, two methods for estimating T1 and T2 independently are of particular relevance:

the first method is the "magnetization-prepared 2 rapid gradient echoes" (MP2RAGE) [4], which uses an inversion pulse to prepare the magnetization in each repetition time (TR), followed by the acquisition of two three-dimensional identical FLASH blocks at different inversion times (TI) (see FIG. 1A), Two images can be reconstructed from one MP2RAGE scan: the short-TI (TI1) blocks result in a T1-weighted and the long-TI (TI2) blocks result in a proton-density-weighted image. A T1 map can be generated by using a combination of these two inversion images and a look-up table (pre-generated with Bloch equation simulations of the specific acquisition scheme) that assigns a T1 value to all possible intensities of the combined image. The MP2RAGE method is generally well suited for high, isotropic resolution T1 mapping of the entire brain as it uses non-selective excitation; and the second method is a T2-prepared rapid gradient echo sequence, called T2PRAGE hereafter. It uses a similar 3D segmented FLASH sequence but with a T2-preparation module [5] (see also U.S. patent publication 2006/0253015 A1) and only one FLASH readout block during the repetition time (instead of two blocks, see FIG. 1B). T2 preparation (T2p) was first introduced by Brittain et al. [6] for imaging the coronary arteries and, generally, consists of a tip-down, refocusing, and tip-up pulses. First, the longitudinal magnetization is tipped on the transverse plane by a 90° pulse, then an echo time ($TE_p$) follows, allowing transversal magnetization to relax (i.e., dephase). During this period, a series of 180° refocusing pulses is used to create a coherent transversal magnetization (echo) at the end of $TE_p$, when the magnetization is tipped back up onto the longitudinal axis with a −90° pulse. Thus, T2 relaxation effects are imprinted into the longitudinal magnetization before imaging. In other words, after this procedure, the available longitudinal magnetization is scaled according to the T2 relaxation occurred during $TE_p$. The FLASH readout block typically implements a center-out k-space trajectory ordering to encode the T2-prepared contrast in the first readouts close to the k-space center. The resulting image has a T2 weighting depending on $TE_p$. A T2 map (i.e., a spatial representation of the T2 tissue property) can be obtained with this method by acquiring at least two images with different $TE_p$ and applying a voxel-wise fit of the mono-exponential signal equation:

$$M_{TEp} = M_0 e^{-\left(\frac{TE_p}{T2}\right)},$$

where $M_0$ indicates the longitudinal magnetization at $TE_p=0$ ms [7,8].

SUMMARY OF THE INVENTION

It is an objective of the present invention to find a system and method capable of simultaneously mapping MRI parameters such as T1, T2, and other tissue- or system-specific parameters like proton density or field inhomogeneity that overcome the above-mentioned disadvantages (i.e. notably limitations in accuracy, acquisition time, and experimental bias) and are suitable for clinical applications.

The objective is achieved according to the present invention by a system and method for simultaneous mapping of qMRI parameters using a T2 prepared inversion according to the object of the independent claims. Dependent claims present further advantages of the invention.

The present invention proposes notably a qMRI method for mapping one or several qMRI parameters of a biological object with an MRI system, capable of simultaneously mapping several of the qMRI parameters. The method includes the following steps of:

performing, byr the MRI system, N scans C_1, ... , C_N, with N≥1, wherein each scan C_j, with j=1, ... , N, comprises:

performing one or several magnetization preparation radio frequency (hereafter "RF") pulse series, each followed by M_j readout blocks (i.e. the scan C_j comprises, after each magnetization preparation RF pulse series, a number M_j of readout blocks. Wherein the number M_j for scan C_j might be different from the number of readout blocks used for another of the scans. Optionally, for all scan, a same number of readout blocks follows each magnetization preparation RF pulse series). Wherein two successive magnetization preparation RF pulse series are separated by a repetition time interval TR_j (i.e. two different scans might use each a different repetition time interval depending on the number of readout blocks after each magnetization preparation RF pulse series, all repetition time intervals between two successive magnetization preparation RF pulse series of a same scan being the same), wherein each magnetization preparation RF pulse series is a T2-prepared inversion pulse series comprising multiple pulses. Preferentially, it comprises the following series of successive RF pulses: a tip-down pulse, followed by, optionally, a pair of refocusing pulses, and ending with a tip-down pulse. The series of successive pulses is notably configured for creating a T2 contrast on the transverse plane during the magnetization preparation and restoring longitudinal magnetization on the negative (ending tip-down) z-axis in order to generate T1 recovery entangled with T2 prepared contrast. Each magnetization preparation RF pulse series according to the invention is characterized by an echo time, $TE_{p\_}j$, i.e. first to last inter-pulse duration, wherein the MRI system is configured for varying said echo time $TE_{p\_}j$, i.e. the duration of the latter, notably within a same scan (i.e. the echo time $TE_{p\_}j$ takes different values for each of the magnetization preparation RF pulse series of a same scan) and/or for each scan (i.e. the echo time $TE_{p\_}j$ takes an identical value for all magnetization preparation RF pulse series of a same scan, but said identical value is different for each scan), for obtaining different T2 weightings. In other words, the MRI system is preferentially configured for varying the echo time $TE_{p\_}j$ within the same scan, notably if N=1, so that each magnetization preparation RF pulse series of said same scan is characterized by a different echo time $TE_{p\_}j$ and/or for varying the echo time $TE_{p\_}j$ between different scans, so that the echo time $TE_{p\_}j$ characterizing the magnetization preparation RF pulse series of a scan is different from the echo time $TE_{p\_}j$ characterizing the magnetization preparation RF pulse series of the other scans, notably of all other scans. Preferentially, if N>1, each scan is characterized by a unique echo time $TE_{p\_}j$ characterizing (i.e. being the same for) all magnetization preparation RF pulse series of the considered scan, that is at the same time different from the echo time $TE_{p\_}j$ characterizing all other scans (i.e. the echo time $TE_{p\_}j$ is unique within each scan, but is different for each scan). The notation "$TE_{p\_}j$" refers to an inter-pulse duration used for the scan C_j. As mentioned above, for a same scan, the magnetization preparation RF pulse series of said same scan might be characterized each by an echo time $TE_{p\_}j$ whose value is different from the value of the echo time $TE_{p\_}j$ of all other magnetization preparation RF pulse series of said same scan. The T2-prepared inversion pulse series is notably configured for inverting the longitudinal magnetization and for creating a T2-weighted recovery signal by generating translational relaxation before longitudinal inversion so that an acquired MRI recovery signal comprises both T1 and T2 weighting components. Preferentially, the T2-prepared inversion pulse series is an adiabatic T2-prepared inversion pulse series containing two tip-down RF pulses temporally framing two refocusing RF pulses. In particular, the adiabatic T2-prepared inversion pulse series contains the following series of temporally successive pulses: a first pulse that is a rectangular tip-down RF pulse, followed successively by a second pulse, a third pulse, and finally a fourth pulse, wherein the second and third pulses are both hyperbolic-secant-refocusing adiabatic RF pulses, and the fourth pulse is also a rectangular tip-down RF pulse. Preferentially, the first and fourth pulses are substantially identical, and the second and third pulses are also substantially identical. Of course, other adiabatic or non-adiabatic pulses can be used instead of the hyperbolic secant pulse previously mentioned as well as other adiabatic or non-adiabatic pulses may be used for tip-down instead of rectangular pulses. Preferentially, the inter-pulse duration $TE_{p\_}j$ between the first pulse and the fourth pulse (i.e. the echo time of the T2-prepared inversion pulse series) is different for each scan C_j or even each repetition time interval TR_j in order to obtain different T2 weightings. Preferentially, the duration between the two refocusing pulses, e.g. between the second and third pulse, is equal to $TE_p/2$. Preferentially, the duration between the first and second pulse is equal to $TE_p/4$. The above-mentioned durations are notably measured from one pulse center (i.e. middle of pulse) to another pulse center (i.e. middle of pulse), wherein each pulse center is defined with respect to the width of the considered pulse;

an acquisition, by the MRI system and during each readout block, of the MRI recovery signal generated by at least a part of the biological object, wherein for each readout block R_i,j, an MRI signal S_i,j is acquired by the MRI system at a different inversion time TI_i,j, with i=1, ... , M_j, and M_j≥2;

reconstructing, for and from each MRI signal S_i,j, an image of I_i,j of the part;

creating a voxel-wise signal by concatenating intensity values of a same voxel of the reconstructed images. In other words, when considering the different reconstructed images I_i,j, a same voxel, representing thus a same position within the imaged biological part throughout the reconstructed images, will be associated to different intensity values in function of the different inversion times TI_i,j and inter-pulse durations $TE_{p\_j}$, one intensity value for each reconstructed images. The present invention proposes thus to collect, for the same voxel, the intensity value provided by each of the reconstructed images, the same voxel having thus different intensity values in function of the different parameter couples (TI_i,j;$TE_{p\_j}$). The voxel-wise signal can then be obtained by plotting for each voxel the intensity value of the voxel obtained in function of each couple (TI_i,j;$TE_{p\_j}$) with i=1, . . . , M_j and j=1, . . . , N, and ordering for instance the intensity values according to predefined criterion, e.g. from the first acquired intensity value to the last acquired intensity value. For instance, after completion of the N scans C_1, . . . , C_N, the voxel-wise signal is created by concatenating M_j×N intensity values of the same voxel of the reconstructed images of the N successive scans. Alternatively, a single scan (N=1) can be performed by the MRI system by interleaving a combination of L different inter-pulse durations $TE_{p\_j}$ and M_j inversion times TI_i,1 resulting in multiple T1 and T2 sensitizations within the single scan, the latter producing therefore as many images as there are TI_i,1, i.e. M_j images associated with TEp_j, times the number of different $TE_p$, i.e. L. In such a case, the voxel-wise signal is created by concatenating the M_j×L intensity values of the same voxel of the reconstructed images as explained before;

fitting a physical model to the concatenated intensity values to obtain at least one qMRI map of one of said qMRI parameters. For instance, the system according to the invention can be configured for performing a numerical simulation of each scan C_j, wherein said numerical simulation is configured for generating, for each voxel, a set of simulated voxel-wise signals and, for providing, for each simulated voxel-wise signal, a value for one or several qMRI parameters, e.g. T1, T2, B1+, etc. Each simulated voxel-wise signal provides an intensity value for a concerned voxel in function of different values of (TI_i,j;$TE_{p\_j}$). The set of simulated voxel-wise signals might be defined as a dictionary that will be used for quantitative map reconstruction using "dictionary fitting" as explained below, wherein for each simulated voxel-wise signal, a "look-up table" provides the corresponding values for said one or several qMRI parameters. Preferentially, a physics-based model is used for creating the simulated voxel-wise signal, wherein said physics-based model preferentially uses extended-phase-graph (EPG), or Bloch-Equations, or analytical solutions [9]. Then the system according to the invention can be configured for reconstructing, for at least one of the gMRI parameter, a quantitative map representing the imaged biological part by matching, for each voxel of the map, the created voxel-wise signal of the corresponding voxel in the reconstructed images and all simulated voxel-wise signals generated for the voxel, and assigning to the considered voxel in the quantitative map the value of the at least one qMRI parameter for which the best match has been obtained.

In other words, the invention proposes thus a qMRI method using a novel magnetization prepared rapid gradient echo approach coupled preferentially with a dictionary matching method for quantitative parameter maps reconstruction. Contrary to the first method described above, i.e. the MP2RAGE sequence which uses a simple inversion for its magnetization preparation module, the present invention proposes to use a modified T2-prepared inversion module (T2pi) to invert the longitudinal magnetization while encoding T2 contrast in the subsequent T1 recovery. Contrary to the second method, i.e. the T2PRAGE sequence, the present invention proposes to use two or more readouts, and not only one.

The present invention concerns also an MRI system or apparatus configured for simultaneous mapping of one or several qMRI parameters of a biological object by carrying out the steps of the previously described method. The MRI system contains for instance:

an axial magnetic field coil and an axial magnetic field coil controller for controlling an axial magnetic field $B_0$ generated by the axial magnetic field coil;

a gradient coil and a gradient coil controller configured for controlling a magnetic field gradient G generated by the gradient coil;

a RF coil and a RF coil controller configured for controlling a RF magnetic field B1 produced by the RF coil;

a receiver coil, which can be the same as the RF coil, configured for detecting changes in a magnetization of a biological object to be imaged, and for communicating the changes to a receiver coil controller, which can be the same as the RF coil controller, the latter outputting an MRI signal to a processing unit containing a processor, the processing unit being configured for processing the outputted MRI signal in order to reconstruct images of the biological object;

a display for displaying the reconstructed images;

characterized in that the processing unit is configured for automatically carrying out the previously described method.

The foregoing has broadly outlined the features and technical advantages of the present disclosure so that those skilled in the art may better understand the detailed description that follows.

Additional features and advantages of the disclosure will be described hereinafter that form the object of the claims. Those skilled in the art will appreciate that they may readily use the concept and the specific embodiment disclosed as a basis for modifying or designing other structures for carrying out the same purposes of the present disclosure.

Other features which are considered as characteristic for the invention are set forth in the appended claims.

Although the invention is illustrated and described herein as embodied in a method and a system for simultaneous mapping of quantitative MRI parameters using a T2 prepared inversion, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 1A:
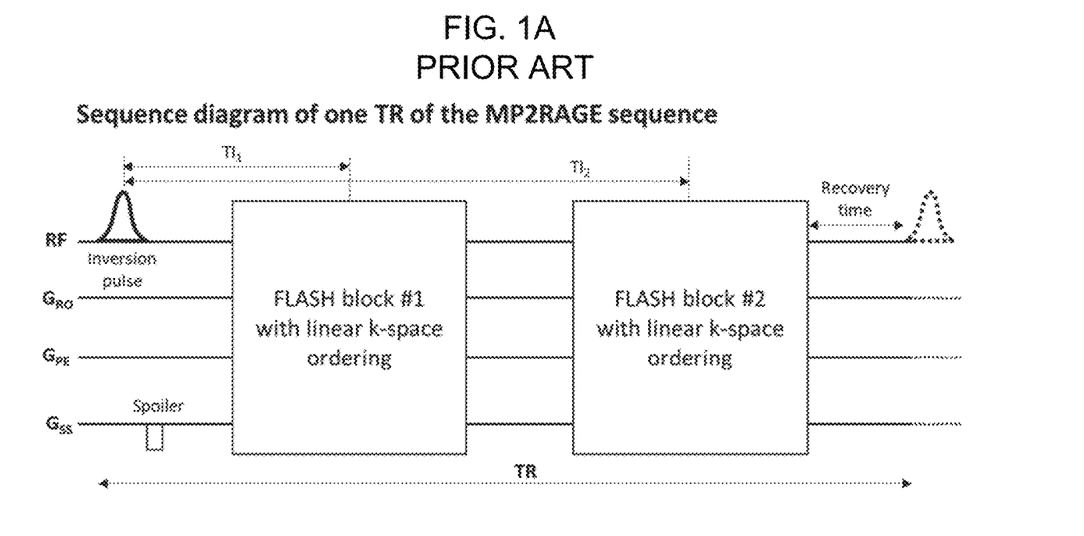
FIG. 1A is a schematic illustration of an MP2RAGE pulse sequence according to the prior art.
Figure 1B:
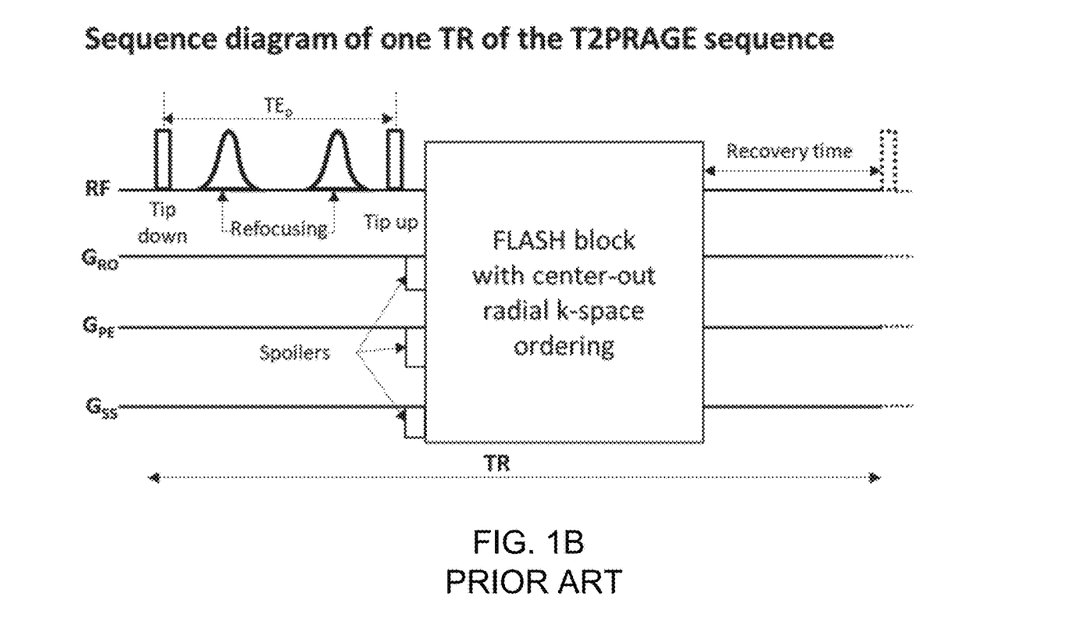
FIG. 1B is a schematic illustration of a T2PRAGE pulse sequence according to prior art.

Referring now to the figures of the drawings in detail and first, particularly to FIGS. 1A and 1B thereof, there is shown known pulse sequences which include an MP2RAGE pulse sequence (A) and a T2PRAGE pulse sequence (B) which have been described respectively with the so-called first method and second method. These pulse sequences are known in the art sequences and do not need further description here.

Figure 2:
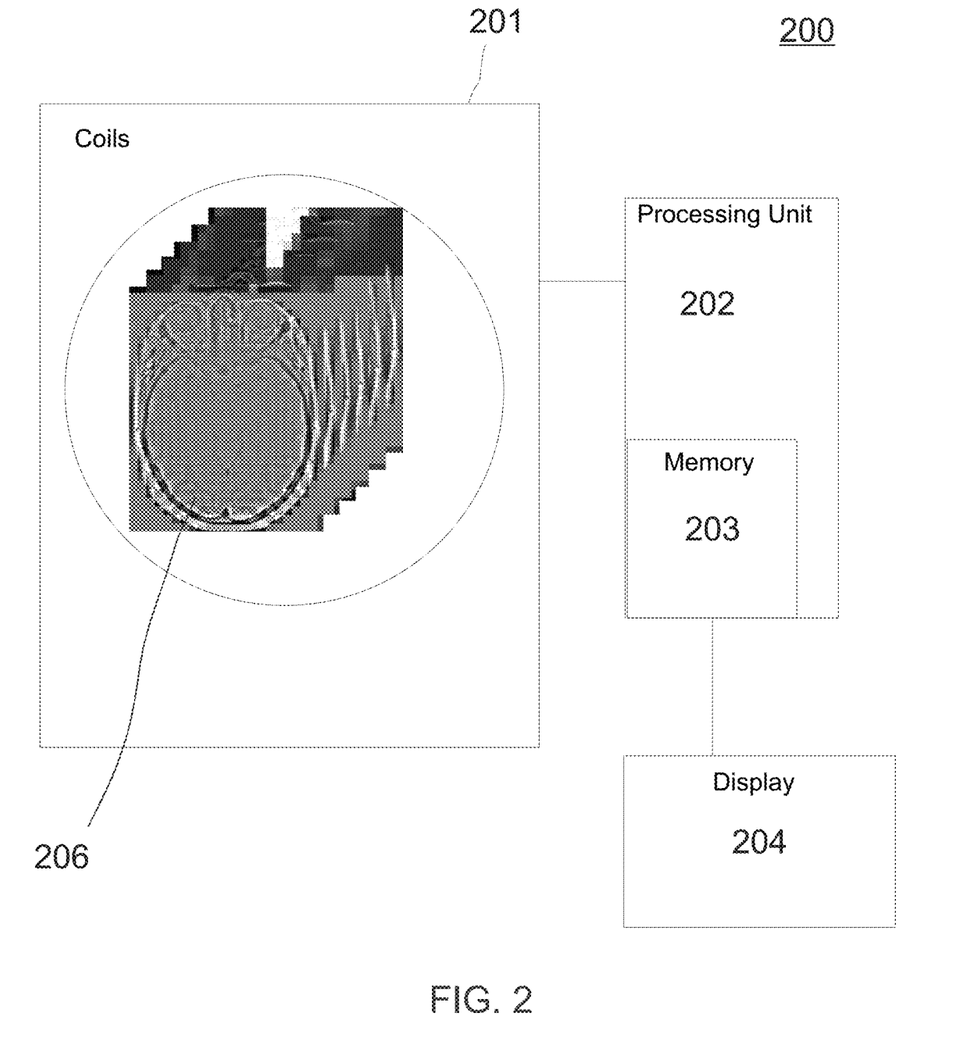
FIG. 2 is a schematic illustration of an MRI system according to the invention.
Figure 3:
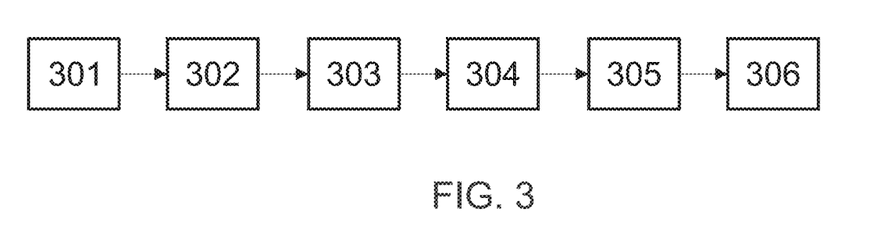
FIG. 3 is a flowchart showing a method for qMRI mapping according to the invention.

FIG. 2 schematically illustrates an MRI system 200 according to the invention. As known in the art, the MRI system 200 contains different coils 201 and respective coil controllers configured for generating magnetic fields and RF pulses in order to acquire an MRI signal from a biological object 206. The MRI signal is transmitted by a receiver coil controller to a processing unit 202 containing typically a memory 203 and connected to a display 204 for displaying images reconstructed from the received MRI signal. Contrary to prior art MRI systems, the MRI system 200 according to the invention is configured for carrying out the following method described in connection with FIGS. 3 to 5.

Figure 4:
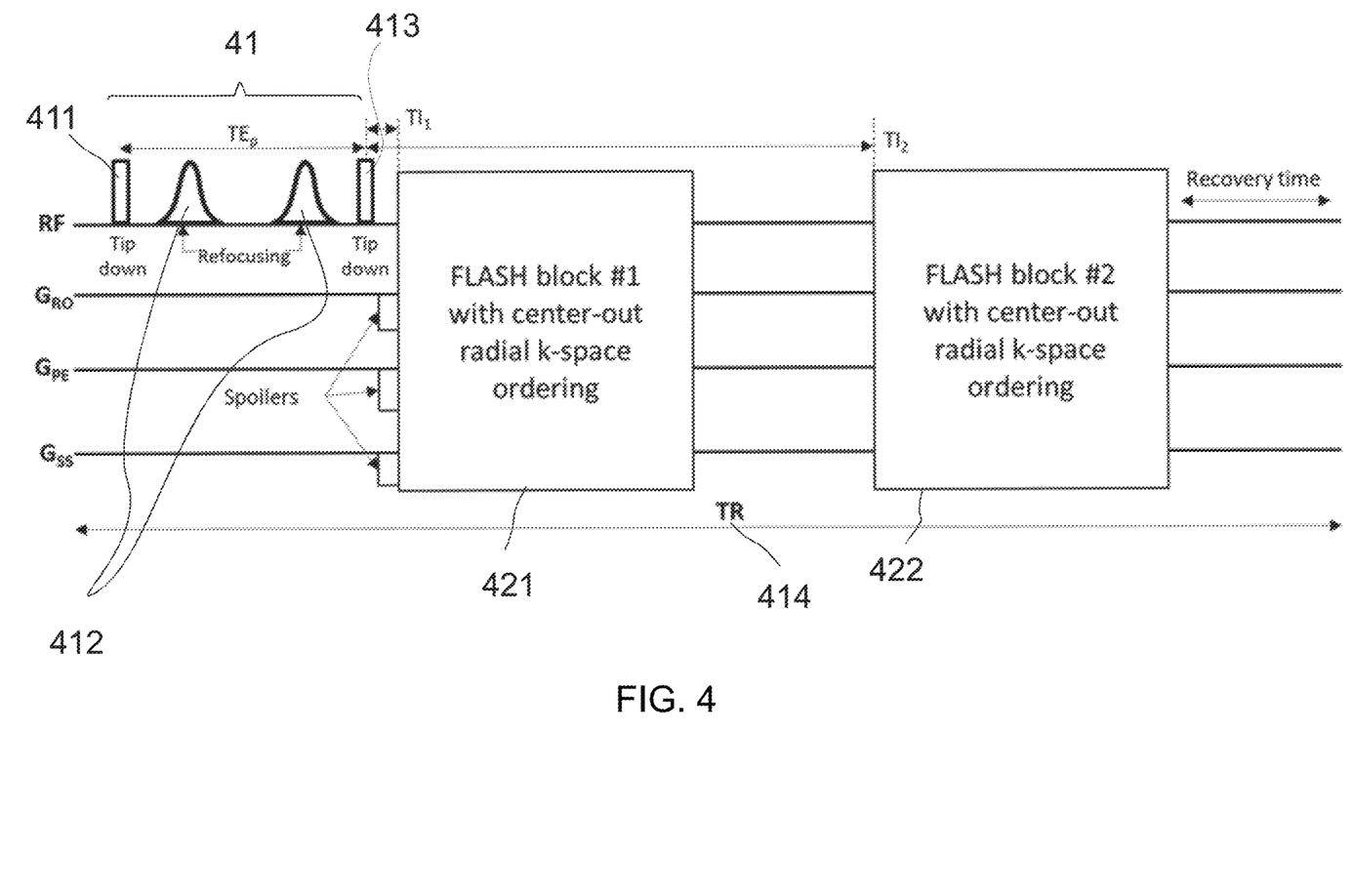
FIG. 4 is a schematic illustration showing an adiabatic T2-prepared inversion pulse series according to the invention.

At step 301, the MRI system 200 performs one or several scans with C_j, with j=1, . . . , N, of the biological object 206. For each scan, the MRI system 200 performs, at step 302, one or several T2-prepared inversion pulse series characterized each by an echo time, i.e. inter-pulse duration, $TE_p\_j$, wherein the inter-pulse durations are different within a same scan and/or for each scan. An example of a T2-prepared inversion pulse sequence is provided by FIG. 4 showing one repetition time TR 414 of the sequence. The T2-prepared inversion module 41 (or pulse series) includes notably a first pulse that is a tip-down RF pulse 411, e.g. a rectangular tip-down RF pulse, followed by two successive refocusing pulses 412, e.g. hyperbolic-secant adiabatic refocusing pulses, and ended with a fourth pulse that is also a tip-down RF pulse 413, preferentially a rectangular one. The inter-pulse duration $TE_p\_j$ is measured from the middle of the first pulse width until the middle of the fourth pulse width. A scan comprises multiple TR's to acquire an image. As explained previously, the present invention can be implemented as multiple scans each with a different echo time preparation $TE_p\_j$ or with one single scan that comprises different echo time preparations $TE_p\_j$. In the preferred embodiment shown in FIGS. 4-5, the case of multiple scans is taken as an illustration.

After performing the T2-prepared inversion module 41, the MRI system 200 launches, at step 303, an acquisition of an MRI recovery signal generated by at least a part of the biological object 206. For this purpose, it is configured for generating, for the scan C_j and at different inversion times TI_i,j, with i=1, . . . , M_j with M_j≥2, and before starting a next scan, M_j readout 421, 422 RF excitation pulse sequences configured for applying a RF magnetic field B1 to the part of the biological, and for detecting and acquiring for each of the M_j readout excitation pulse sequences, thus for each of the different inversion times TI_i,j and in response to the application of the RF magnetic field B1, an MRI recovery signal S_i,j. In particular, each inversion time defines the time interval between the end of the T2-prepared inversion module 41 and the start of the corresponding readout RF excitation pulse sequence, i.e. readout block. The latter is for instance a segmented 3D MRI pulse sequence (e.g., FLASH [10]) employing an accelerated k-space sampling pattern [11]. A non-limiting illustration of an acquisition of the MRI recovery signal is shown in FIG. 4, wherein two readout blocks, i.e. M_j=2, are acquired in each repetition time interval TR at different inversion times TI_1,j and TI_2,j after the T2-prepared inversion pulse sequence 41. For each of the readout blocks, a center-out radial k-space ordering is used for encoding the prepared T2 contrast at the center of k-space. As known in the art, the slice-select gradient GSS, the in-plane phase-encoding gradient GPE and the readout (frequency-encoding) gradient GRO are controlled according to the specific type of readout block that is used, e.g. FLASH.

Figure 5:
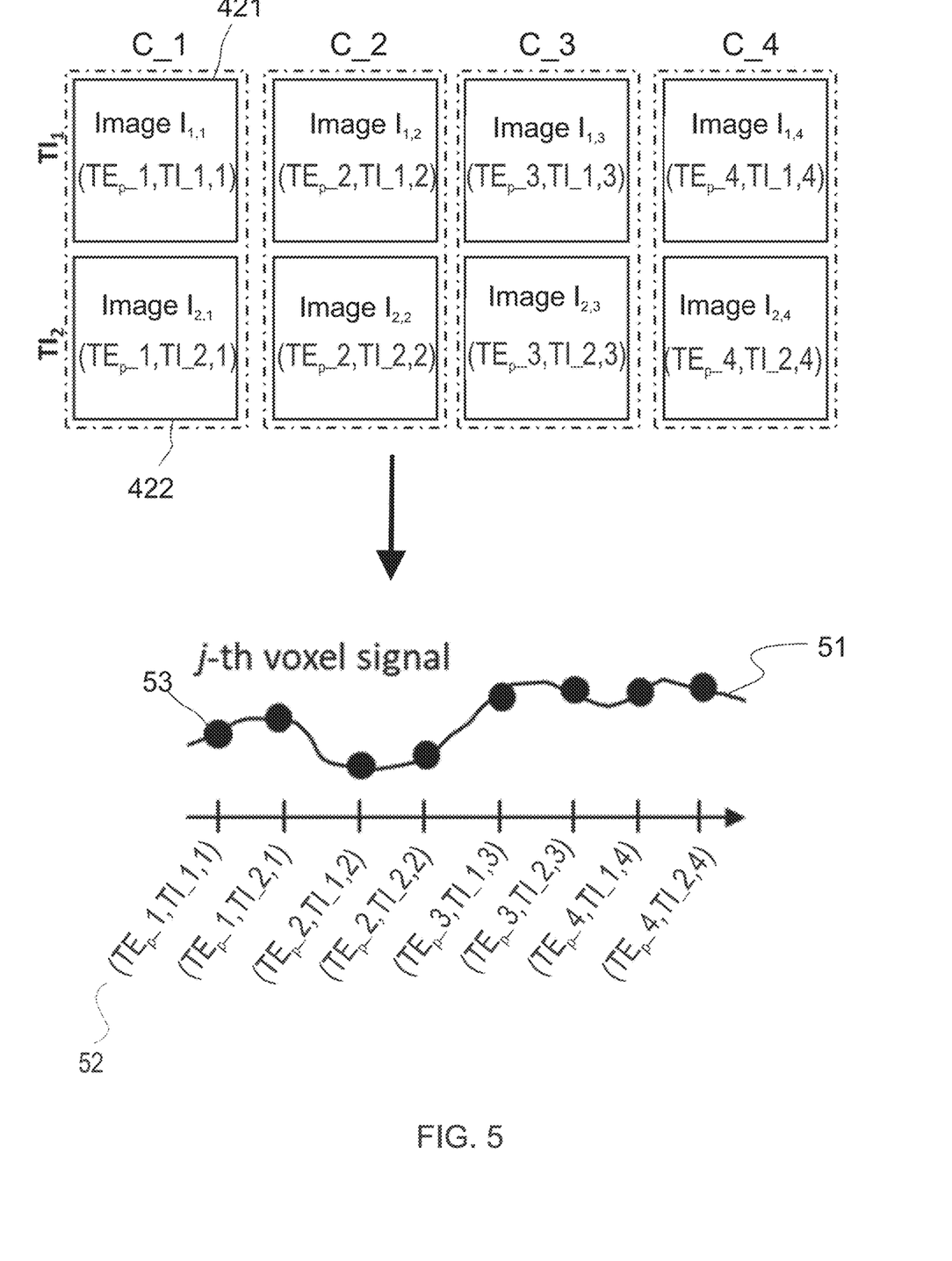
FIG. 5 is a schematic illustration of a creation of a voxel-wise signal according to the invention.

FIG. 5 illustrates a case where four scans C_j (i.e. N=4) were temporally successively performed, preferentially with the pulse sequence shown in FIG. 4, i.e. with M_j=M=2 readout blocks 421, 422 for j=1, . . . , N, i.e. according to a first inversion time $TI_1$ and a second inversion time $TI_2$. Each scan C_j, with j=1, . . . , 4 combines thus different $TE_p$'s and TI's to probe a wide range of T2 and T1 contrasts. In particular, scan C_1 and C_2 use short echo times $TE_p$, with $TE_p\_1 < TE_p\_2$ with shortest possible inversion times TI_1,1 and TI_1,2 and medium long second inversion times TI_2,1 and TI_2,2, i.e. TI_2,1>TI_1,1 and TI_2,2>TI_1,2, with for instance TI_1,1=TI_1,2 and TI_2,1=TI_2,2. Scan C_3 and C_4 uses longer echo times $TE_p$, i.e. with $TE_p\_2 < TE_p\_3 < TE_p\_4$, shortest possible first inversion time, e.g. TI_1,1=TI_1,3=TI_1,4 and a longer second inversion time, i.e. TI_2,3>TI_2,2 and TI_2,4>TI_2,2, or TI_2,3>TI_2,1 and TI_2,4>TI_2,1, with preferentially TI_2,3=TI_2,4. In particular, TI_2,3 and TI_2,4 are strictly greater than any of the inversion times TI_2,1 and TI_2,2, which are also strictly greater than any of the inversion times TI_1,1, TI_1,2, TI_1,3, and TI_1,4.

At step 304, the MRI system, for instance its processing unit 202, is configured for reconstructing, from each received MR signal S_i,j, an image I_i,j of the biological object part under investigation. For instance, each scan C_1, . . . , C_4 shown in FIG. 4 provides two 3D images, respectively one image at the first inversion time $TI_1$ and another image at the second inversion time $TI_2$, resulting in overall eight images with different $T_1$ and $T_2$ weighting. Each image might be reconstructed using a compressed sensing algorithm [12]. Of course, other known in the art fast reconstruction methods or algorithm may also be suited for individual image reconstruction (e.g., parallel imaging, AI based, machine learning- or deep learning-based implementation, etc).

Preferentially, to account for biases due to B1 transmit field inhomogeneities, an additional, fast B1+ map might be acquired by the MRI system according to the invention.

At step 305, the MRI system creates a voxel-wise signal from the intensity values that are provided by the different reconstructed images for a same voxel. Preferentially, the intensity values are concatenated to obtain the voxel-wise signal. In other words, the MRI system is configured for collecting, in each reconstructed image, the intensity value that is associated to the voxel that represents the same position within the imaged part of the biological object (i.e. for each voxel of a reconstructed image, the intensity value associated to the concerned voxel in the reconstructed image and the intensity value associated to the same voxel in all other reconstructed images are collected and associated to said voxel, i.e. to a position within the imaged part). This enables to construct or create, for each voxel, the voxel wise signal 51 as shown in FIG. 5. The latter associates to each couple of time values ($TE_p\_j, TI\_i,j$) 52, i.e. to each image, the intensity value 53 that has been obtained for the considered voxel in that image, i.e. for that couple of time values. Preferentially, the MRI system might automatically concatenate the intensity values 53 to obtain said voxel-wise signal 51.

At step 306, the MRI system, preferentially its processing unit, or another processing unit not part of the MRI system, e.g. a stand-alone computer, is configured for fitting a physical model to the concatenated intensity values 53 to obtain at least one quantitative map. For instance, the MRI system might be configured for performing a numerical simulation of each scan $C\_j$, more precisely, of each of the voxel-wise acquired signals. This might be performed before step 301, i.e. before starting the scanning process, or during the scanning process. The numerical simulation is configured for generating, for each of the voxels, a set of simulated voxel-wise signals, associating, to each of the simulated voxel-wise signals, a value for one or several qMRI parameters, e.g. the corresponding value for T1, T2, B1+ for the considered voxel. The set of simulated voxel-wise signals might populate a "dictionary" that can be used for imaging the biological part. In particular, different algorithms or physics-based models for estimating the qMRI parameters and simulating the acquired voxel-wise signals might be used, like EPG or conventional Bloch equations simulation.

Then, the MRI system, preferentially its processing unit or the another processing unit, might be configured for performing a reconstruction, for at least one of the qMRI parameters, of a quantitative map representing the part of the biological object. For generating the quantitative map, the processing unit is configured for matching, for each voxel of the quantitative map, the created voxel-wise signal defined for that voxel and all simulated voxel-wise signals generated for that voxel, and assigning to the considered voxel in the quantitative map the value of the at least one qMRI parameter for which the best match has been obtained. The obtained quantitative MRI map might then be displayed on the display 204.

Preferentially, said fast B1+ map might be used for selecting the simulated voxel-wise signals which are associated to B1+ values that match the acquired B1+ value for the considered voxel. In particular, "matching" means that the difference between the intensity values of the acquired voxel wise signal or acquired parameter (e.g. B1+) and the intensity values of the simulated voxel wise signal or simulated parameter (e.g. B1+) is smaller than a predefined value. It has to be understood that different known techniques might be used for finding the best match between the simulated voxel-wise signals and the acquired one, for instance by using dot-product, RMSE, etc.

In general, the invention preferentially comprises at least 2, but up to N scans with different $TE_p$ and at least two but up to $M\_j$ readout blocks for each scan $C\_j$, with different TIs, where $M\_j$, N, $TE_p$'s, and TIs are optimized to trade off accuracy of target T1 and T2 ranges with acquisition time. Thanks to the present invention, T1 and T2 maps might be simultaneously estimated/reconstructed from the voxel-wise "dictionary fitting" using the resulting magnitude images and optionally the B1+ map. In alternative to dictionary fitting, a model-based approach, which employs a physics model within the reconstruction, can be used to obtain quantitative maps directly from the acquired k-space.

To summarize, the present invention proposes a combination of a T2-prepared inversion module (or pulse sequence), notably the use of a tip-down/refocusing/tip-down pulse series, with a segmented readout sequence that includes multiple readout blocks following the magnetization preparation, i.e. said T2-prepared inversion pulse module. Using arbitrary combinations of T2 preparation ($TE_p$ times) and inversion times result in images whose contrast depend on both T1 and T2. Finally, these images can be used as input to an algorithm that construct the voxel-wise signal for each voxel and compares the latter to simulated voxel-wise signals which are each associated to qMRI parameters like T1 or T2 in order to construct a quantitative map of the qMRI parameter(s) from the best matching. This enables notably to construct simultaneously a T1 and T2 quantitative map.

Compared to T1 or T2 quantification techniques like MP2RAGE or T2-prepared rapid gradient echo sequences that estimate one relaxation parameter at the time, the advantage of the present invention is that it makes possible to include both T1 and T2 relaxation parameters in the signal model, minimizing therefore measurement bias from relaxation mechanisms different than the one being probed. Compared to other simultaneous T1/T2 quantification techniques like DESPOT1/2 or MRF, the advantage of the invention consists of using a simple signal model and a conventional acquistion technology (e.g., Cartesian k-space sampling, magnetization preparation, FLASH readout sequences) that is well supported by current scanner hardware, readily available for clinical use and, more specifically, well suited for high isotropic resolution imaging with large volumetric coverage.

Advantageously, the proposed method further provides a lower sensitivity to B1+ inhomogeneity than the above-mentioned known in the art techniques, because of the low flip-angle readout out blocks, and a lower SAR compared to other T2 mapping methods like MESE based methods.

Without departing from the general concept of the present invention, different radio-frequency pulses for the T2-prepared inversion pulse sequence can be used, as long as said T2-prepared pulse sequence performs a T2-weighted inverted longitudinal magnetization before the readout blocks. Therefore, different adiabatic pulses like AFP, BIR4, etc., might be used for the tip-down or the refocusing in the T2-prepared inversion pulse sequence. In general, T2-prepared inversion scans could also be combined with conventional T2-prepared scans that employ tip-down/refocusing/tip-up pulse series using short or long inter-pulse duration $TE_p$.

Also, different qMRI parameters, other than or in addition to T1, T2, can be probed by modifying the T2-prepared inversion pulse sequence and then subsequently estimated in the reconstruction, like relaxation times T1ρ, T2ρ, magnetization transfer, diffusion, B1+, perfusion, fat and/or water fraction, etc. In particular, T2' relaxation time could be estimated with the proposed invention by using a modified T2-preparation where the timings of the refocusing pulses are changed and made asymmetrical with respect to the middle of the tip-down inter-pulse duration (i.e. resulting in an uncomplete refocusing of the transverse magnetization), for instance for two refocusing pulses, by setting theft timings at TEp/12 and TEp/4 (uncomplete refocusing) instead of TEp/4 and 3*TEp/4 (refocused).

Similarly, while the described method proposes to an additional B1+ map to mitigate bias from transmit field inhomogeneity, other maps might be used to take other effects into account if necessary, like B1−, B0 frequency offset, diffusion, etc.

Preferentially, for the k-space sampling, the proposed method uses a variable-density Cartesian trajectory based on the spiral phyllotaxis pattern [13] and undersampled in phase- and slice-encoding dimensions. Of course, other k-space sampling strategies might be used, like hybrid Cartesian-radial trajectories like stack-cif-stars, "kooshball" 3D radial, 2D spiral, 3D variable density "cones" spirals, etc. In particular, different k-space ordering than the radial-like previously described can be used.

Advantageously, the method according to the invention might use different acquisition strategies, like 2D, 3D slab-selective, 3D non-selective, and different sequence types for the readout blocks of the acquisition, Ike FLASH, bSSFP, etc.

Preferentially, different metrics for dictionary fitting than a cross-product between absolute quantities can be used, like calculating a minimum root mean square error or an absolute difference.

Finally, while the method described a preferred embodiment based on a dictionary fitting procedure, other techniques for matching experimental data with simulated data, e.g. with a physics-based model, can be used to estimate the relaxation parameters (e.g., the physics-based model can be embedded in the reconstruction of the input images to output directly quantitative maps).

To conclude, this invention proposes a qMRI method that simultaneously estimates multiple tissue MR parameters, including but not limited to T1 and T2 relaxation times, using at least two read-out blocks (e.g., FLASH or bSSFP type) after a T2-prepared inversion coupled with a physics-based numerical model/simulation for the reconstruction of quantitative maps.

The following is a summary list of reference numerals and the corresponding structure used in the above description of the invention.

LIST OF ABBREVIATIONS

MRI magnetic resonance imaging
MR magnetic resonance
qMRI quantitative magnetic resonance imaging
TA acquisition time
MRF magnetic resonance fingerprinting
TI inversion time
$TE_p$ echo time
RF radio frequency
TR repetition time

LIST OF CITATIONS

[1] Deoni S C, Rutt B K, Peters T M. Rapid combined T1 and T2 mapping using gradient recalled acquisition in the steady state. Magn Reson Med 2003; 49(3):515-526.
[2] Ma D, Gulani V, Seiberlich N, Liu K, Sunshine J L, Duerk J L, Griswold M A. Magnetic resonance fingerprinting. Nature 2013; 495(7440):187-192.
[3] Mugler J P, 3rd, Brookeman J R. Three-dimensional magnetization-prepared rapid gradient-echo imaging (3D MP RAGE). Magn Reson Med 1990; 15(1):152-157
[4] Marques J P, Kober T, Krueger G, van der Zwaag W, Van de Moortele P F, Gruetter R. MP2RAGE, a self bias-field corrected sequence for improved segmentation and T1-mapping at high field. Neuroimage 2010; 49(2):1271-1281.
[5] Nezafat R, Stuber M, Ouwerkerk R, Gharib A M, Desai M, Pettigrew R I. B1 insensitive T2 preparation for improved coronary magnetic resonance angiography at 3T. Magn Reson Med 2006; In Press.
[6] Brittain J H, Hu B S, Wright G A, Meyer C H, Macovski A, Nishimura D G. Coronary angiography with magnetization-prepared T2 contrast. Magn Reson Med 1995; 33(5):689-696.
[7] Giri S, Chung Y C, Merchant A, Mihai G, Rajagopalan S, Raman S V, Simonetti O P. T2 quantification for improved detection of myocardial edema. J Cardiovasc Magn Reson 2009; 11:56.
[8] van Heeswijk R B, Feliciano H, Bongard C, Bonanno G, Coppo S, Lauriers N, Locca D, Schwitter J, Stuber M. Free-breathing 3 T magnetic resonance T2-mapping of the heart. JACC Cardiovasc Imaging 2012; 5(12): 1231-1239.
[9] Cloos M A, Knoll F, Zhao T, Block K T, Bruno M, Wiggins G C, Sodickson D K. Multiparametric imaging with heterogeneous radiofrequency fields. Nat Commun 2016; 7:12445.
[10] Frahm J, Haase A, Matthaei D. Rapid NMR imaging of dynamic processes using the FLASH technique. Magn Reson Med 1986; 3(2):321-327.
[11] Forman C, Piccini D, Grimm R, Hutter J, Hornegger J, Zenge M O. High-resolution 3D whole-heart coronary MRA: a study on the combination of data acquisition in multiple breath-holds and 1D residual respiratory motion compensation. MAGMA 2014.
[12] Wetzl J, Forman C, Wintersperger B J, D'Errico L, Schmidt M, Mailhe B, Maier A, Stalder A F. High-resolution dynamic CE-MRA of the thorax enabled by iterative TWIST reconstruction. Magn Reson Med 2017; 77(2):833-840.
[13] Forman C, Piccini D, Grimm R, Hutter J, Hornegger J, Zenge M O. High-resolution 3D whole-heart coronary MRA: a study on the combination of data acquisition in multiple breath-holds and 1D residual respiratory motion compensation. MAGMA 2014.

The invention claimed is:
1. A quantitative magnetic resonance imaging (qMRI) method for mapping at least one qMRI parameter of a biological object with an MRI system, the method comprises the following steps:
performing, by the MRI system, N scans C_1, . . . , C_N, wherein each scan C_j, with j=1, . . . , N, includes:
performing at least one magnetization preparation radio frequency (RF) pulse series, each followed by M_j readout blocks, wherein two successive said magnetization preparation RF pulse series are separated by a repetition time interval TR_j, wherein each said magnetization preparation RF pulse series is a T2-prepared inversion pulse series containing multiple pulses and characterized by an echo time, being an inter-pulse duration, $TE_{p\_j}$, wherein the inter-pulse duration is a time between first and last pulses, and is varied by the MRI system in order to obtain different T2 weightings, the at least one magnetization preparation RF pulse series being configured for inverting a longitudinal magnetization while encoding T2 contrast in a subsequent T1 recover;

acquiring, by the MRI system and during each readout block, an MRI recovery signal generated by at least a part of the biological object, wherein for each said readout block R_i,j, an MRI signal S_i,j is acquired by the MRI system at a different inversion time TI_i,j, with i=1, . . . , M_j, and M_j≥2;

reconstructing, for and from each said MRI signal S_i,j, an image I_i,j of the part;

creating a voxel-wise signal by concatenating intensity values obtained for a same voxel for reconstructed images; and fitting a physical model to concatenated intensity values to obtain at least one qMRI map of the at least one qMRI parameter.

2. The qMRI method according to claim 1, wherein the echo time $TE_{p\_j}$ takes different values for each of the magnetization preparation RF pulse series of a same scan, or an identical value for all the magnetization preparation RF pulse series of the same scan, the identical value being different for each said scan.

3. The qMRI method according to claim 1, wherein the fitting is a dictionary fitting which comprises the further steps of:

performing a numerical simulation of each said scan C_j, wherein the numerical simulation is configured for generating, for each voxel, a set of simulated voxel-wise signals and, for providing, for each simulated voxel-wise signal, a value for the at least one qMRI parameter; and reconstructing, for the at least one gMRI parameter, a quantitative map representing an imaged biological part by matching, for each voxel of the quantitative map, a created voxel-wise signal of a corresponding voxel in reconstructed images and all simulated voxel-wise signals generated for the voxel, and assigning to a considered voxel in the quantitative map the value of the at least one qMRI parameter for which a best match has been obtained.

4. The qMRI method according to claim 3, which further comprises using a physics-based model for creating the simulated voxel-wise signal.

5. The qMRI method according to claim 3, which further comprises acquiring an additional map for selecting the set of simulated voxel-wise signals to be matched with an acquired voxel-wise signal.

6. The qMRI method according to claim 5, wherein the additional map is selected from the group consisting of:

a B1+ map;
a B1− map;
a B0 frequency offset map; and
a diffusion map.

7. The qMRI method according to claim 1, wherein the T2-prepared inversion pulse series is adiabatic or non-adiabatic.

8. The qMRI method according to claim 7, wherein the T2-prepared inversion pulse series is an adiabatic T2-prepared inversion pulse sequence containing two tip-down RF pulses temporally framing two refocusing adiabatic RF pulses, wherein a time interval between a middle of a first tip-down RF pulse of the two tip-down RF pulses and a middle of a last tip-down RF pulse of the two tip-down RF pulses is the inter-pulse duration $TE_{p\_j}$.

9. The qMRI method according to claim 8, wherein the adiabatic T2-prepared inversion pulse sequence contains a following series of temporally successive pulses including:

a first pulse that is a rectangular tip-down RF pulse, followed successively by a second pulse, a third pulse, and finally a fourth pulse, wherein the second and third pulses are both hyperbolic-secant-refocusing adiabatic RF pulses, and the fourth pulse is a rectangular tip-down RF pulse.

10. The qMRI method according to claim 1, wherein the voxel-wise signal is obtained by plotting for each voxel an intensity value of the voxel obtained in function of each couple (TI_i,j; $TE_{p\_j}$).

11. The qMRI method according to claim 1, which further comprises selecting the at least one qMRI parameter from the group consisting of:

a T1 relaxation time;
a T2 relaxation time;
a T2* and/or T2' relaxation time;
a B1+ RF field;
a proton density;
a T1p and/or T2p relaxation time;
a magnetization transfer parameter;
a diffusion parameter;
a perfusion parameter; and
a fat and/or water fraction parameter.

12. The qMRI method according to claim 1, wherein the physical model uses extended-phase-graph, or Bloch-Equations, or analytical solutions.

13. A magnetic resonance imaging system configured for carrying out the qMRI method according to claim 1.

* * * * *

UNITED STATES PATENT AND TRADEMARK OFFICE
CERTIFICATE OF CORRECTION

| | | |
|---|---|---|
| PATENT NO. | : 12,336,802 B2 | Page 1 of 1 |
| APPLICATION NO. | : 18/300604 | |
| DATED | : June 24, 2025 | |
| INVENTOR(S) | : Gabriele Bonanno et al. | |

It is certified that error appears in the above-identified patent and that said Letters Patent is hereby corrected as shown below:

In the Claims

Claim 3, Column 13, Lines 30-38 should read as follows:
reconstructing, for the at least one qMRI parameter, a
    quantitative map representing an imaged biological
    part by matching, for each voxel of the quantitative
    map, a created voxel-wise signal of a corresponding
    voxel in reconstructed images and all simulated voxel-
    wise signals generated for the voxel, and assigning to
    a considered voxel in the quantitative map the value of
    the at least one qMRI parameter for which a best match
    has been obtained.

Signed and Sealed this
Second Day of September, 2025

Coke Morgan Stewart
*Acting Director of the United States Patent and Trademark Office*